US010004877B2

United States Patent
Tegg

(10) Patent No.: US 10,004,877 B2
(45) Date of Patent: *Jun. 26, 2018

(54) DEFLECTABLE CATHETER SHAFT SECTION, CATHETER INCORPORATING SAME, AND METHOD OF MANUFACTURING SAME

(71) Applicant: St. Jude Medical, Atrial Fibrillation Division, Inc., St. Paul, MN (US)

(72) Inventor: Troy T Tegg, Elk River, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 743 days.

This patent is subject to a terminal disclaimer.

(21) Appl. No.: 13/836,846

(22) Filed: Mar. 15, 2013

(65) Prior Publication Data
US 2013/0296780 A1 Nov. 7, 2013

Related U.S. Application Data
(60) Provisional application No. 61/643,748, filed on May 7, 2012.

(51) Int. Cl.
*A61M 25/01* (2006.01)
*A61B 18/14* (2006.01)
(Continued)

(52) U.S. Cl.
CPC ......... *A61M 25/0147* (2013.01); *A61B 18/14* (2013.01); *A61M 25/0026* (2013.01);
(Continued)

(58) Field of Classification Search
CPC .......... A61M 25/0147; A61M 25/0144; A61M 25/0136; A61M 2025/015;
(Continued)

(56) References Cited

U.S. PATENT DOCUMENTS 6,198,974 B1 * 3/2001 Webster, Jr. ...... A61M 25/0136
600/146
7,465,288 B2 12/2008 Dudney et al.
(Continued)

FOREIGN PATENT DOCUMENTS

CN 101528145 A 9/2009
CN 101708130 A 5/2010
(Continued)

OTHER PUBLICATIONS

International Search Report and Written Opinion; International Searching Authority of the European Patent Office, dated Oct. 16, 2013.

*Primary Examiner* — Nathan R Price
*Assistant Examiner* — Melissa A Snyder
(74) *Attorney, Agent, or Firm* — Dykema Gossett PLLC

(57) ABSTRACT

A deflectable catheter shaft section is disclosed comprising an elongated body extending along a longitudinal axis and comprising a distal end and a proximal end; and a plurality of lumens extending along the longitudinal axis of the elongated body, wherein at least one of the lumens is abutting at least another one of the lumens. A catheter comprising the deflectable catheter shaft section and a method of manufacturing the deflectable catheter shaft section are also disclosed. A catheter incorporating a deflectable catheter shaft section can further comprise first and second compression coils disposed over pull wires located within the catheter, wherein the compression coils are unattached to the catheter or components thereof, but can be constrained by a shaft coupler at a distal end of each of the compression coils and by at least a portion of a handle assembly at a proximal end of each of the compression coils.

22 Claims, 17 Drawing Sheets

(51) Int. Cl.
*A61M 25/00* (2006.01)
*A61B 5/042* (2006.01)
*A61B 18/00* (2006.01)
*A61B 5/00* (2006.01)
*A61B 5/01* (2006.01)

(52) U.S. Cl.
CPC .... *A61M 25/0136* (2013.01); *A61M 25/0144* (2013.01); *A61B 5/01* (2013.01); *A61B 5/042* (2013.01); *A61B 5/6852* (2013.01); *A61B 18/1492* (2013.01); *A61B 2018/00821* (2013.01); *A61B 2018/00839* (2013.01); *A61B 2217/007* (2013.01); *A61M 25/0009* (2013.01); *A61M 2025/0059* (2013.01); *A61M 2025/015* (2013.01); *Y10T 29/49863* (2015.01)

(58) Field of Classification Search
CPC .. A61M 2025/0059; A61M 2025/0037; A61M 25/0026; A61M 25/0141; A61M 25/0032
See application file for complete search history.

(56) References Cited

U.S. PATENT DOCUMENTS

| | | | |
|---|---|---|---|
| 7,815,635 B2 | 10/2010 | Wittkampf et al. | |
| 7,998,141 B2 | 8/2011 | Wittkampf et al. | |
| 8,016,784 B1 | 9/2011 | Hayzelden et al. | |
| 8,162,934 B2 | 4/2012 | Potter | |
| 8,187,267 B2 | 5/2012 | Pappone et al. | |
| 8,206,404 B2 | 6/2012 | de la Rama et al. | |
| 8,287,533 B2 | 10/2012 | Wittkampf et al. | |
| 8,480,669 B2 | 7/2013 | Pappone et al. | |
| 8,715,279 B2 | 5/2014 | de la Rama et al. | |
| 8,734,440 B2 | 5/2014 | Wu | |
| 8,790,341 B2 | 7/2014 | Pappone et al. | |
| 8,827,910 B2 | 9/2014 | de la Rama et al. | |
| 2002/0165461 A1 | 11/2002 | Hayzelden et al. | |
| 2005/0070844 A1 | 3/2005 | Chow et al. | |
| 2005/0070894 A1 | 3/2005 | McClurken | |
| 2006/0264820 A1* | 11/2006 | Ponzi | A61B 18/1492 604/95.04 |
| 2007/0270679 A1* | 11/2007 | Nguyen | A61M 25/0043 600/373 |
| 2007/0270791 A1 | 11/2007 | Wang et al. | |
| 2008/0114335 A1* | 5/2008 | Flickinger | A61M 25/01 604/523 |
| 2009/0012517 A1 | 1/2009 | de la Rama et al. | |
| 2009/0163913 A1 | 6/2009 | Wang et al. | |
| 2010/0015273 A1 | 1/2010 | Akaki et al. | |
| 2010/0030114 A1 | 2/2010 | Nguyen et al. | |
| 2010/0152731 A1 | 6/2010 | de la Rama et al. | |
| 2011/0288392 A1 | 11/2011 | de la Rama et al. | |
| 2011/0313417 A1 | 12/2011 | De La Rama et al. | |
| 2012/0130217 A1 | 5/2012 | Kauphusman et al. | |
| 2012/0130218 A1 | 5/2012 | Kauphusman et al. | |
| 2012/0265130 A1 | 10/2012 | de la Rama et al. | |
| 2012/0283552 A1 | 11/2012 | Hall et al. | |
| 2013/0085479 A1 | 4/2013 | de la Rama et al. | |
| 2013/0296781 A1 | 11/2013 | Tegg et al. | |
| 2014/0330269 A1 | 11/2014 | Pappone et al. | |
| 2014/0343546 A1 | 11/2014 | de la Rama et al. | |
| 2015/0107766 A1 | 4/2015 | Tegg et al. | |
| 2015/0352327 A1 | 12/2015 | Helgeson et al. | |
| 2016/0192982 A1 | 7/2016 | Just et al. | |

FOREIGN PATENT DOCUMENTS

| | | |
|---|---|---|
| EP | 1033107 A1 | 9/2000 |
| EP | 2327365 A1 | 6/2011 |
| EP | 2347726 A1 | 6/2011 |
| EP | 2347720 A2 | 7/2011 |

* cited by examiner

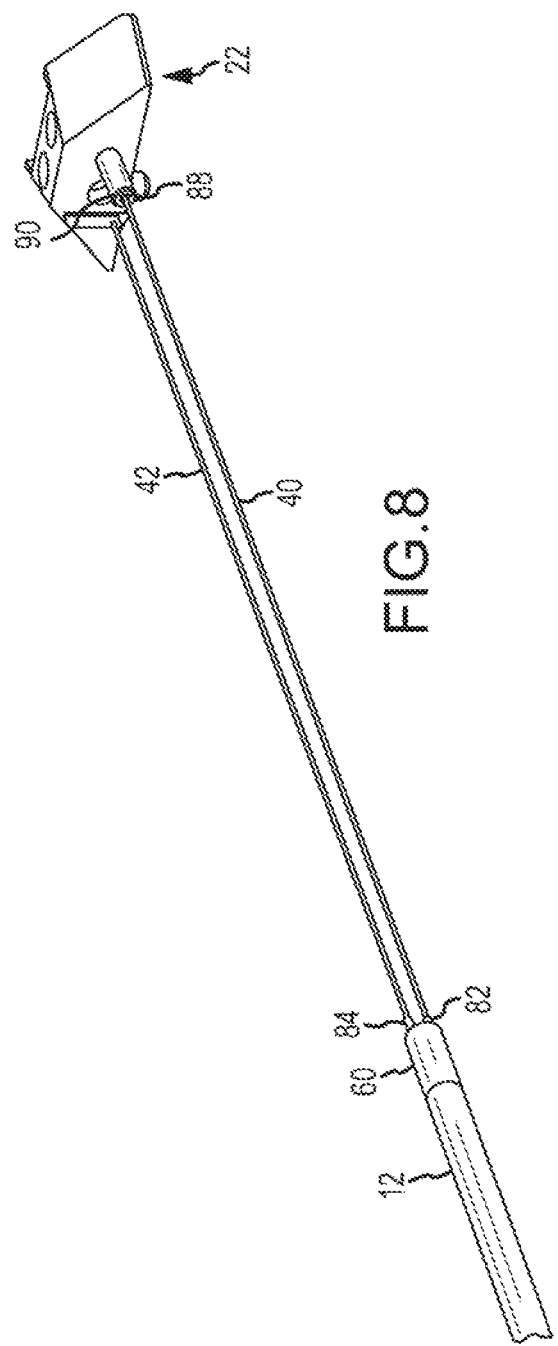

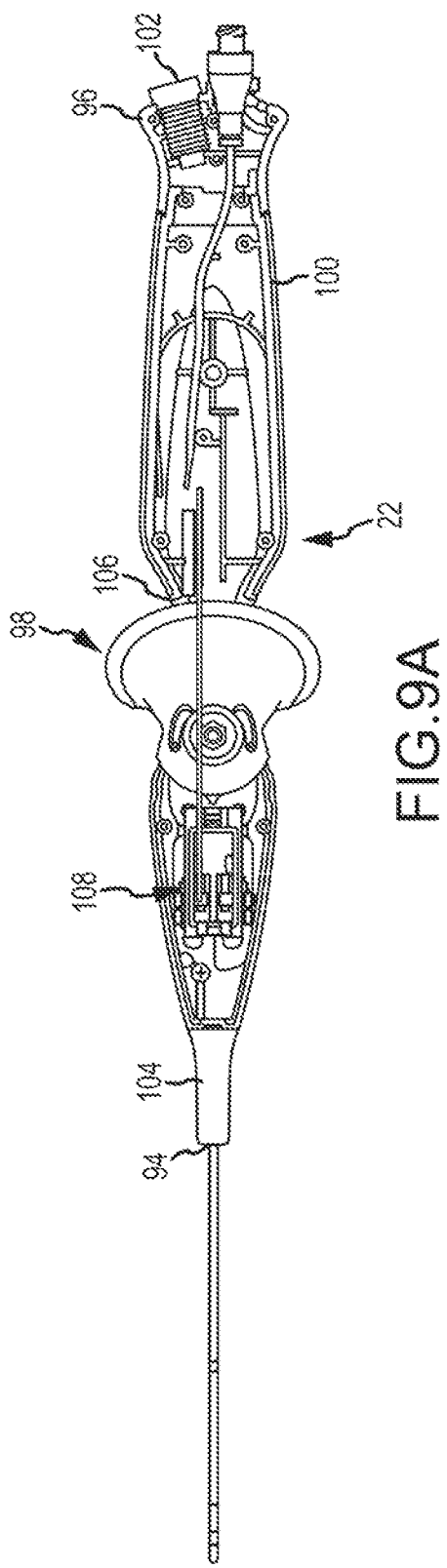

DEFLECTABLE CATHETER SHAFT SECTION, CATHETER INCORPORATING SAME, AND METHOD OF MANUFACTURING SAME

CROSS-REFERENCE TO RELATED APPLICATION

This application claims the benefit of U.S. provisional application No. 61/643,748, filed 7 May 2012 (the '748 application), which is hereby incorporated by reference as though fully set forth herein. This application is related to United States nonprovisional application Ser. No. 13/838,124, filed 15 Mar. 2013, now U.S. Pat. No. 8,814,825, issued 26 Aug. 2014.

BACKGROUND OF THE INVENTION a. Field of the Invention

The instant disclosure relates generally to a deflectable catheter shaft section, a catheter incorporating such a deflectable catheter shaft section, and a method of manufacturing such a deflectable catheter shaft section.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a sue within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The proximal end of the catheter can be manipulated to guide the catheter through a patient's vasculature. The distal tip can be deflected by a pull wire attached at the distal end of the catheter that extends to a control handle that controls the application or tension on the pull wire.

Two of the mechanical considerations for a catheter shaft are that it transmit torque and resist compression during use. With respect to transmitting torque, medical personnel normally navigate the distal end of the catheter to a desired location in part by manipulating a handle disposed at the proximal end of the catheter. Substantial frictional forces sometimes resist transmission of torque across the length of the catheter. In some cases, these threes can cause the catheter shaft to twist about a longitudinal axis of the catheter shaft, storing energy in the process in a spring-like fashion. If the energy is released suddenly, the distal end of the catheter, which may be deflected by a steering mechanism, can be undesirably propelled with significant force.

With respect to resisting, compression during use, it is important liar medical personnel to be able to advance the catheter through a vessel, sometimes against significant frictional resistance, without undue axial compression or snaking of the catheter shaft. Shaft compression can result in a loss of control tier the medical practitioner and can complicate the positioning of the distal end of the catheter shaft at a desired location for a medical procedure. In addition, medical personnel may rely on tactile feedback to attain and verify proper positioning, of the catheter, and such feedback can be impaired by excessive compressibility.

The foregoing discussion is intended only to illustrate the present field and should not be taken as a disavowal of claim scope.

BRIEF SUMMARY OF THE INVENTION

In various embodiments, a deflectable catheter shaft section can comprise an elongated body extending along a longitudinal axis and comprising a distal end and a proximal end; and a plurality of lumens extending along the longitudinal axis of the elongated body, wherein at least one of the plurality of lumens is abutting at least another one of the plurality of lumens. Each of the plurality of lumens can be abutting at least another one of the plurality of lumens in embodiments of the invention. The deflectable catheter shaft section can further comprise a plurality of liners corresponding to each of the plurality of lumens, wherein each of the plurality of liners is comprised of polytetrafluoroethylene (PTFE). Each of the plurality of lumens can be less than about 0.015 inches from another of the plurality of lumens in accordance with some embodiments of the invention.

In various embodiments, a catheter can comprise a deflectable catheter shall section comprising an elongated body extending along a longitudinal axis and comprising a distal end and a proximal end; and a plurality of lumens extending along the longitudinal axis of the elongated body, wherein at least one of the plurality of lumens is abutting at least another one of the plurality of lumens; and a proximal catheter shaft section disposed at the proximal end of the deflectable catheter shaft section. Each of the plurality of lumens can be abutting at least another one of the plurality of lumens in embodiments of the invention. Each of the plurality of lumens can be less than about 0.015 inches from another of the plurality of lumens in accordance with some embodiments of the invention. The catheter can further comprise a plurality of liners corresponding to each of the plurality of lumens of the deflectable catheter shaft section, wherein each of the plurality of liners is comprised of PTFE.

In at least one embodiment, the deflectable catheter shaft section can comprise a first pocket located at the distal end and a second pocket located at the proximal end. The catheter can further comprise a tip assembly disposed at the distal end of the deflectable catheter shaft section in the first pocket and a handle assembly comprising an actuator configured to effect movement of the deflectable catheter shaft section. The catheter can further comprise a pull ring disposed in the first pocket and at least two pull wires attached to diametrically opposite locations on the pull ring, wherein the pull wires extend from the pull ring toward the handle assembly. The catheter can further comprise a shaft coupler disposed in the second pocket. The shaft coupler can be generally cylindrical in shape and can comprise an outer radial surface comprising a helical groove.

In at least one embodiment, the catheter can further comprise first and second compression coils each disposed over one of the at least two pull wires, wherein each of the first and second compression coils comprises a proximal end and a distal end, wherein the distal end of each of the first and second compression coils abuts and is constrained by the shaft coupler, and wherein the proximal end of each of the first and second compression coils abuts and is constrained by at least a portion of the handle assembly. The first and second compression coils can be unattached to the proximal catheter shaft section. The first and second compression coils can be unattached to the shaft coupler. The first and second compression coils can be unattached to the handle assembly.

In various embodiments, a method of manufacturing a deflectable catheter shaft section can comprise the steps of providing a plurality of mandrels; providing a mandrel alignment tool comprising a plurality of slots, each of the plurality of slots configured for housing at least a portion of one of the plurality of mandrels; placing a plurality of first polymeric tubes over the plurality of mandrels; providing tooling configured to hold the mandrel alignment tool, wherein the tooling comprises a plurality of pairs of opposing tensioning blocks, each of the plurality of pairs of opposing tensioning blocks corresponding to one of the plurality of mandrels or the mandrel alignment tool, and wherein each of the plurality of pairs of opposing tensioning, blocks is configured to place one of the plurality of mandrels under tension and release one of the plurality of mandrels from tension; attaching each of the plurality of mandrels and each of the plurality or first polymeric tubes to one of the plurality of pairs of opposing tensioning blocks; tensioning each of the plurality of mandrels; and releasing tension of each of the plurality of mandrels. In accordance with an embodiment of the invention, the step of providing a mandrel alignment tool comprising a plurality of slots comprises wire cutting from one of the plurality of slots to another of the plurality of slots. In accordance with an embodiment of the invention, each of the plurality of first polymeric tubes comprises PTFE.

In at least one embodiment, the method of manufacturing a deflectable catheter shaft section can further comprise the steps of placing a cylindrical braid structure over the plurality of mandrels and the plurality of first polymeric tubes; stretching the cylindrical braid structure; and placing at least one second polymeric tube over the cylindrical braid structure. In accordance with an embodiment of the invention, the at least one second polymeric tube comprises polyurethane, nylon, or polyether block amides.

In at least one embodiment, the method of manufacturing a deflectable catheter shaft section can further comprise the steps of placing a heat shrink tube over the at least one second polymeric tube so that the heat shrink tube covers at least a portion of the mandrel alignment tool; subjecting the tooling, the plurality of mandrels, the plurality of first polymeric tubes, the cylindrical braid structure, the at least one second polymeric tube, and the heat shrink tube to a heating process; and reflowing at least a portion of the deflectable catheter shall section. In accordance with an embodiment of the invention, the method of manufacturing a deflectable catheter shaft section can further comprise the step of pre-shrinking the heat shrink tube, wherein the step of pre-shrinking the heath shrink tube can comprise applying; heat with a heat gun. The method of manufacturing a deflectable catheter shaft section can further comprise the steps of: removing the plurality of mandrels; removing the heat shrink tube; and trimming at least a portion of the deflectable catheter shaft section to a select length.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 8 is a schematic view of a portion of the deflectable catheter shall section of FIG. 1, pull wires, and a portion of a handle assembly in accordance with an embodiment of the invention.

FIG. 9A is a partially cut-away, top view of a handle assembly for a catheter incorporating the deflectable catheter shaft section of FIG. 1 in accordance with an embodiment of the invention.

DETAILED DESCRIPTION OF THE DISCLOSURE

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however that the embodiments may be practiced without such specific details. In other instances, well-known operations, components, and elements have not been described hi detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
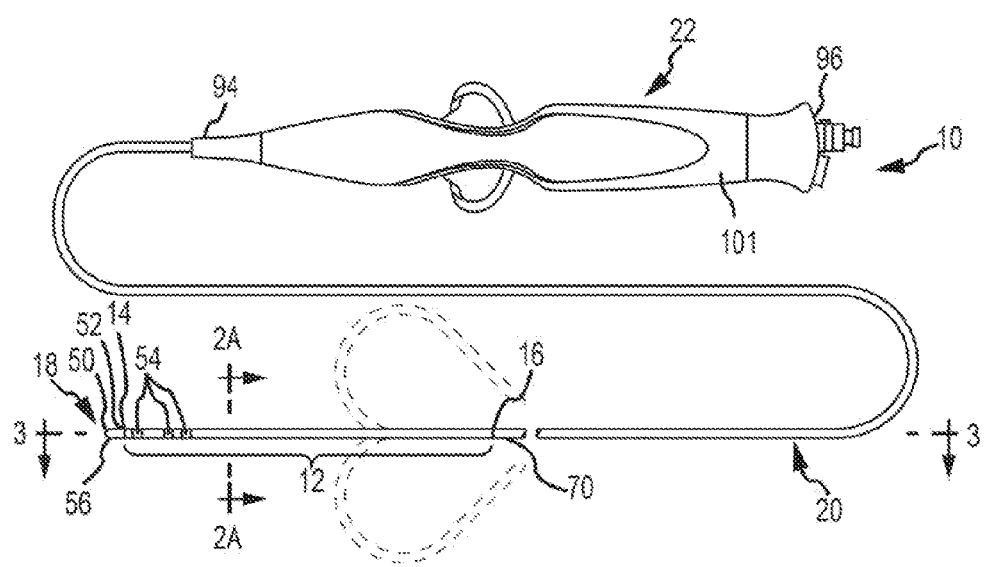
FIG. 1 is a schematic view of a catheter incorporating a deflectable catheter shall section in accordance with an embodiment of the invention.

FIG. 1 generally illustrates a deflectable electrophysiology catheter 10 that comprises a deflectable catheter shaft section 12 in accordance with an embodiment of the invention. Deflectable catheter shaft section 12 comprises an elongated body having a distal end 14 and a proximal end 16. In its most general form, catheter 10 further comprises a tip assembly 18 located at the distal end 14 of the deflectable catheter shaft section 12, a proximal catheter shaft section 20 located at the proximal end 16 of the deflectable catheter shaft section 12, and a handle assembly 22. Catheter 10 may be used in any number of diagnostic and therapeutic applications, such as the recording of electrograms in the heart, the performance of a cardiac ablation procedure, and other similar applications/procedures. Accordingly, one of ordinary skill in the art will recognize and appreciate that the inventive deflectable catheter shall section and method of manufacturing the same can be used in any number of diagnostic and therapeutic applications.

Still referring to FIG. 1, deflectable catheter shaft section 12 is disposed between the tip assembly 18 and the proximal catheter shaft section 20. The length and diameter of the deflectable catheter shaft section 12 can vary according to the application. Generally, the length of the deflectable catheter shaft section 12 can range from about 2 inches (50.8 mm) to about 6 inches (152.4 mm) and the diameter of the deflectable catheter shaft section 12 can range from about 5 French to about 12 French. The diameter of the deflectable catheter shaft section 12 can be about 7 French in accordance with some embodiments of the invention. Although these particular dimensions are mentioned in particular, the dimensions of the deflectable catheter shaft section 12 can vary in accordance with various applications of the deflectable catheter shall section 12. The deflectable catheter shaft section 12 can be configured for deflection independent of the proximal catheter shaft section 20.

Figure 2A:
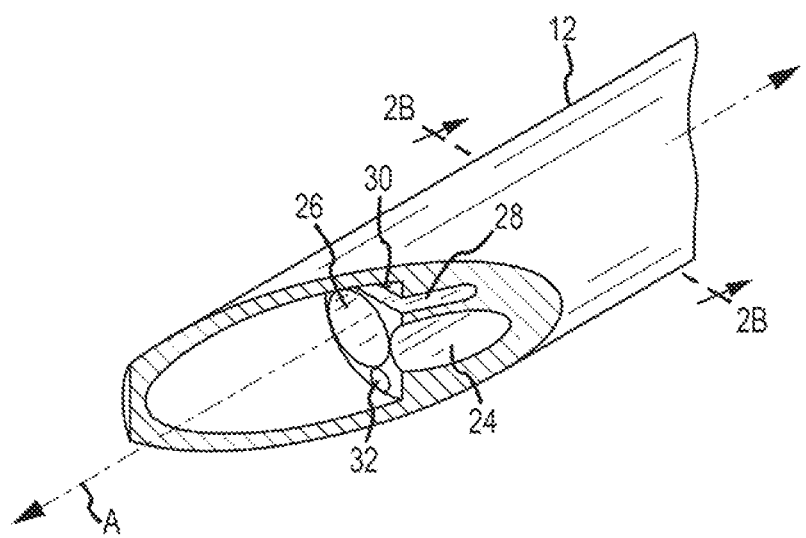
FIG. 2A is a partially cut-away isometric view of the deflectable catheter shaft section of FIG. 1 taken along line 2A-2A, with various components of the catheter omitted for the purposes of clarity.

Referring now to FIG. 2A, deflectable catheter shaft section 12 extends along a longitudinal axis A and comprises at least five substantially separate lumens 24, 26, 28, 30, 32, each extending along the longitudinal axis A from the distal end 14 to the proximal end 16 in accordance with an embodiment of the invention. Each of the plurality of lumens 24, 26, 28, 30, 32 can be fully formed in accordance with an embodiment of the invention, in particular, each of the plurality of lumens can be a desired shape as described hereinbelow. Depending upon the intended application of the catheter 10, each lumen 24, 26, 28, 30, 32 may extend along an entire length of the deflectable catheter shaft section 12 or may extend less than the entire length of the delectable catheter shaft section 12. Each lumen 24, 26, 28, 30, 32 may be formed to have a predetermined cross-sectional profile and shape. Each lumen 24, 26, 28, 30, 32 is configured such that various components required for performing the particular functionality of the catheter 10 (e.g., recording electrograms, ablation, ultrasound, etc.) are disposed therein.

Figure 2B:
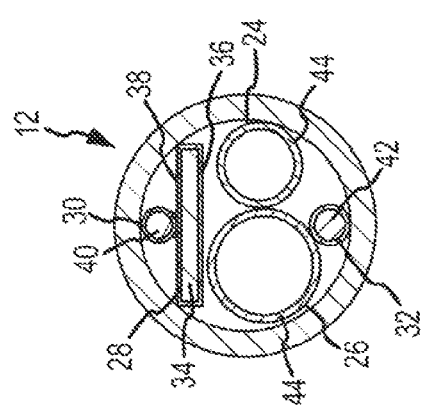
FIG. 2B is a cross-sectional view of the deflectable catheter shaft section of FIG. 1 taken along line 2B-2B seen in FIG. 2A.

Referring now to FIGS. 2A and 2B, first lumen 24 may be generally round in cross-sectional shape. Although this particular shape is mentioned in detail, the cross-sectional shape of the first lumen 24 may vary in accordance with various embodiments of the invention. First lumen 24 may be configured for housing wiring for electrodes as described in more detail hereinbelow or for other electrical components.

Second lumen 26 may be located generally adjacent to or abutting the first lumen 24 within deflectable catheter shall section 12. In accordance with an embodiment of the invention, the first and second lumens 24, 26 may be disposed as proximate each other as manufacturally feasible, while allowing the first and second lumens 24, 26 to be fully formed. For example and without limitation, the distance between first lumen 24 and second lumen 26 may be less than about 0.015 inches (0.38 mm) in accordance with an embodiment of the invention. In an embodiment, the first lumen 24 and the second lumen 26 may be connected to each other. Second lumen 26 may be generally round in cross-sectional shape. Although this particular shape is mentioned in detail, the cross-sectional shape of the second lumen 26 may vary in accordance with various embodiments of the invention. Second lumen 26 may be configured for use as an irrigation fluid passageway and the like.

Third lumen 28 may be located generally adjacent to or abutting both first and second lumens 24, 26. In accordance with an embodiment of the invention, the third lumen 28 and the first and second lumens 24, 26 may be disposed as proximate each other as manufacturally feasible, while allowing the first, second, and third lumens 24, 26, 28 to be fully formed. For example and without limitation, the distance between third lumen 28 and at least one of the first lumen 24 and second lumen 26 may be less than about 0.015 inches (0.38 mm) in accordance with an embodiment of the invention. In an embodiment, the third lumen 28 and at least one of the first lumen 24 and the second lumen 26 may be connected to each other. Third lumen 28 may be generally rectangular in cross-sectional shape. Although this particular shape is mentioned in detail, the cross-sectional shape of the third lumen 28 may vary in accordance with various embodiments of the invention. Third lumen 28 may be configured to house a planarity wire 34 (FIG. 2B). The planarity wire 34 has opposing flat surfaces 36, 38 and is configured to maintain the planarity of the deflectable catheter shaft section 12 as the deflectable catheter shaft section 12 deflects.

Fourth and fifth lumens 30, 32 may be located on opposing sides of the third lumen 28 for the planarity wire 34. The fourth lumen 30 may be located generally adjacent to or abutting the third lumen 28. In accordance with an embodiment of the invention, the third and fourth lumen 28, 30 may be disposed as proximate each other as manufacturally feasible, while allowing the third and fourth lumens 28, 30 to be fully formed. For example and without limitation, the distance between fourth lumen 30 and the third lumen 28 may be less than about 0.010 inches (0.254 mm). In an embodiment, the fourth lumen 30 and the third lumen 28 may be connected to each other. The fifth lumen 32 may be located generally adjacent to or abutting the second lumen 26. In accordance with an embodiment of the invention, the second and fifth lumens 26, 32 may be disposed as proximate each other as manufacturally feasible, while allowing the second and fifth lumens 26, 32 to be fully formed. For example and without limitation, the distance between the fifth lumen 32 and the second lumen 26 may be less than about 0.010 inches (0.254 mm). In an embodiment, the fifth lumen 32 and the second lumen 26 may be connected to each other. The fourth and fifth lumens 30, 32 may be generally round in cross-sectional shape. Although these particular shapes are mentioned in detail, the cross-sectional shape of the fourth and fifth lumens 30, 32 may vary in accordance with various embodiments of the invention. Fourth and fifth lumens 30, 32 may be configured to each house a pull wire 40, 42 (FIG. 2B) to enable the deflectable catheter shaft section 12 to deflect in two or more directions. In particular, the handle assembly 22 described in more detail hereinbelow may comprise at least one pull wire 40, 42 operatively connected to it to facilitate deflection of the deflectable catheter shaft section 12. Although the deflectable catheter shaft section 12 is described and illustrated as including two opposing pull wires 40, 42, it should be noted that the deflectable catheter shaft section 12 of catheter 10 is not limited to two opposing pull wires 40, 42. Rather, the deflectable catheter shaft section 12 of catheter 10 may include a single pull wire arrangement in other embodiments of the invention. The deflectable catheter shaft section 12 of catheter 10 may include more than two pull wires in other embodiments of the invention. The pull wires 40, 42 may be formed from a superelastic nickel-titanium (known as NiTi or Nitinol) wire, carbon fiber, para-aramid synthetic fiber generally available from DuPont under the brand name KEVLAR®, or other suitable material in accordance with various embodiments of the invention. In this configuration of the deflectable shaft section, as shown in FIGS. 2A and 2B, the fourth lumen 30 and the fifth lumen 32 are symmetrically disposed above and below, respectively, an imaginary, longitudinally-extending horizontal plane (not shown) bisecting the deflectable shaft section into an upper hemicylindrical portion and a lower hemicylindrical portion. Similarly, the first lumen 24 and the second lumen 26 are also symmetrically disposed, relative to an imaginary, longitudinally-extending vertical plane (not shown) bisecting the shaft coupler into a left hemicylindrical portion and a right hemicylindrical portion as oriented in FIG. 2A.

Still referring to FIG. 2B, each of the lumens 24, 26, 28, 30, 32 may be lined with liners 44 that serve the purpose of providing a lubricious surface (e.g., to allow for the sliding of the pull wires) and insulating the components within the lumens 24, 26, 28, 30, 32. If provided, the liners 44 may be constructed of a polymeric material, such as PTFE or any other suitable material.

Figure 3:
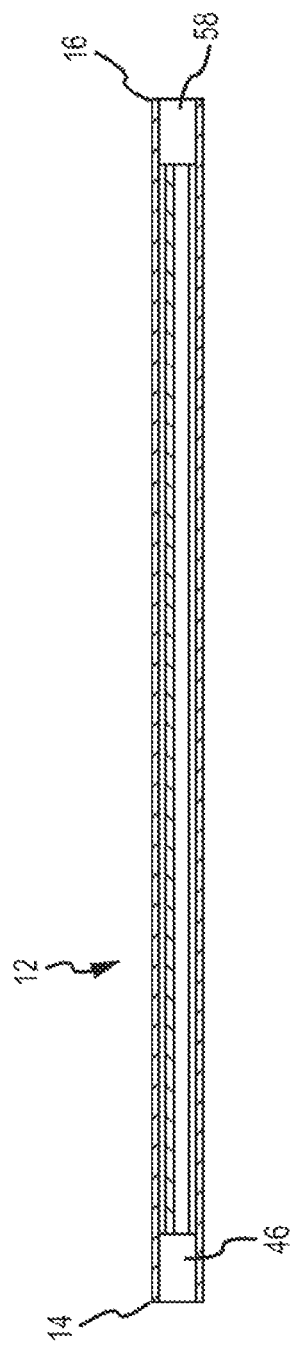
FIG. 3 is a longitudinal, side cross-sectional view of the deflectable catheter shall section of FIG. 1 taken along line 3-3, with various components of the catheter omitted for the purposes of clarity.
Figure 4A:
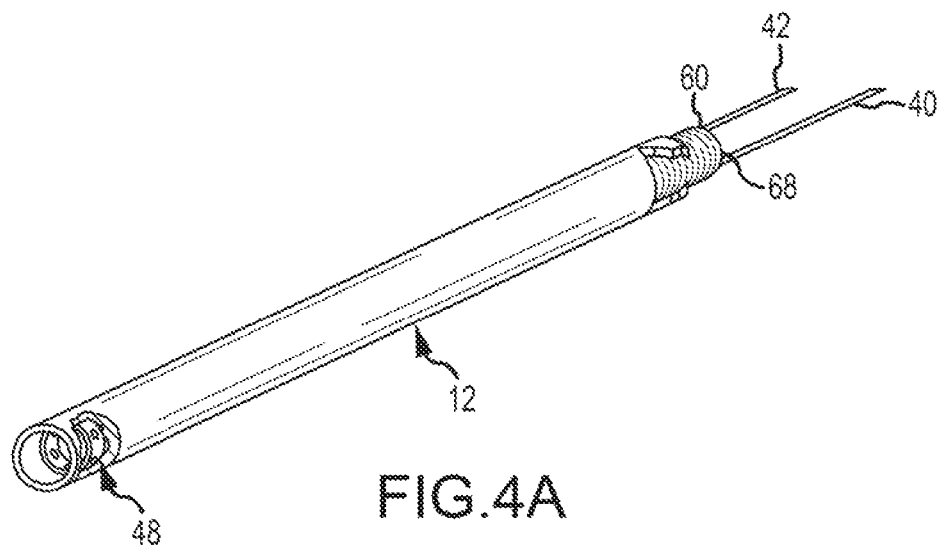
FIG. 4A is a partially cut-away, isometric view of the deflectable catheter shaft section of FIG. 1, showing a shaft coupler in accordance with an embodiment of the invention.

Referring now to FIG. 3, deflectable catheter shaft section 12 comprises a first pocket 46 at distal end 14 configured to accept a pull ring 48 (FIG. 4A). Pull wires 40, 42 are attached to diametrically opposite locations on the pull ring 48 by a solder or weld joint, for example and without limitation. The pull wires 40, 42 then extend from the pull ring 48 toward the handle assembly 22. Pulling of the pull wires 40, 42 by the handle assembly 22 during use of the catheter 10 will cause the pull ring 48 to tilt or rock, thereby deflecting the deflectable catheter shaft section 12. The first pocket 46 at distal end 14 is also configured to accept tip assembly 18.

Referring back to FIG. 1, tip assembly 18 comprises a tip electrode 56 having a distal end 50 and a proximal end 52. Tip electrode 56 may be configured for various functions and may include, without limitation, an active outer surface that is configured for exposure to blood and/or tissue. The tip electrode 56 may be affixed to distal end 14 of the deflectable catheter shaft section 12 in a number of ways. For instance, the tip electrode 56 may be bonded to an inner radial surface of the deflectable catheter shall section 12 using an epoxy material. As used herein, the term "radial surface" means a surface at a radial distance from a central axis or a surface developing uniformly around a central axis (for example, but without limitation, an arcuate surface, an annular surface, or a cylindrical surface). The tip electrode 56 of the tip assembly 18 may have an aperture (not shown) formed therein that is sufficiently sized and configured to receive a wire (not shown) that is connected to the tip electrode 56. One end of the wire is connected to the tip electrode 56 and the other end is connected to, for example, monitoring or recording or ablation devices, such as a radiofrequency (RF) generator. The wire is typically a pre-coated wire that is insulated from other components in the tip assembly 18. The tip electrode 56 of the tip assembly 18 may further include an aperture (not shown) formed therein that is configured to receive a thermocouple (not shown). The thermocouple may be configured to measure the temperature of the tip electrode 56, targeted tissue, and/or the interface therebetween and provide feedback to the monitoring or recording or ablation devices described hereinabove. The tip electrode 56 may further include a fluid lumen configured as a passageway for irrigation fluid.

Figure 4B:
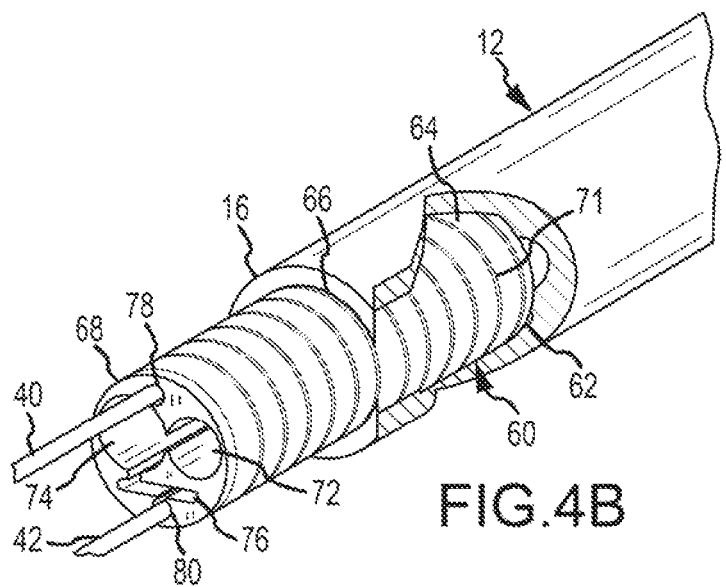
FIG. 4B is a partially cut-away, isometric view of the deflectable catheter shall section of FIG. 1 showing a shall coupler in accordance with an embodiment of the invention.

Referring back to FIG. 3, deflectable catheter shaft section 12 comprises a second pocket 58 at proximal end 16 configured to accept a shaft coupler 60 (FIGS. 4A-4B). Referring to FIGS. 4A-4B, the shaft coupler 60 is configured to connect the deflectable catheter shaft section 12 to the proximal catheter shaft section 20. A distal end 62 of the shaft coupler 60 can be affixed to the proximal end 16 of the deflectable catheter shaft section 12 in a number of ways. For instance, an outer radial surface 64 of the shaft coupler 60 may be bonded to an inner radial surface 66 of the deflectable catheter shaft section 12 using an epoxy material, for example and without limitation. A proximal end 68 of the shaft coupler 60 can be affixed to a distal end 70 (FIG. 1) of the proximal catheter shaft section 20 in a number of ways. For instance, the outer radial surface 64 of the shaft coupler 60 may be bonded to an inner radial surface (not shown) of the proximal catheter shaft section 20 using an epoxy material, for example and without limitation. The outer radial surface 64 of the shaft coupler 60 can comprise a helical groove 71 in accordance with some embodiments of the invention. The helical groove 71 can be configured to have a variable depth in accordance with various embodiments of the invention. The helical groove 71 can be configured to improve bonding between the shaft coupler 60 and the deflectable catheter shaft section 12 in accordance with various embodiments of the invention. For example, in at least one embodiment the groove 71 may be configured to hold an adhesive added during manufacturing of the catheter 10. In another embodiment, the groove 71 may be configured to bond and/or grab onto various portions of the shaft sections 12 and 20 during a reflow process, described in more detail below. In another embodiment, the helical groove 71 may be configured both to hold an adhesive and bond/grab onto the shaft sections 12 and 20 during a reflow process. The shaft coupler 60 can be generally cylindrical in shape. The shaft coupler 60 can also include a plurality of lumens 72, 74, 76, 78, 80 in communication with lumens 24, 26, 28, 30, 32 of deflectable catheter shaft section 12, which function as an electrical lumen, fluid lumen, planarity wire lumen, and pull wire lumens, respectively. In this configuration of the deflectable shaft section and shaft coupler, as shown in FIGS. 4A and 4B, the lumens 78, 80 are symmetrically disposed above and below, respectively, an imaginary, longitudinally-extending horizontal plane (not shown) bisecting the deflectable shaft section and shaft coupler into an upper hemicylindrical portion and a lower hemicylindrical portion. Similarly, the lumens 72, 74 are also symmetrically disposed, relative to an imaginary, longitudinally-extending vertical plane (not shown) bisecting the deflectable shaft section and shaft coupler into a left hemicylindrical portion and a right hemicylindrical portion as oriented in FIGS. 4A and 4B. The connected lumens 72, 74 further define a figure eight cross-sectional shape which defines a waist where the first and second lumens connect.

Figure 5:
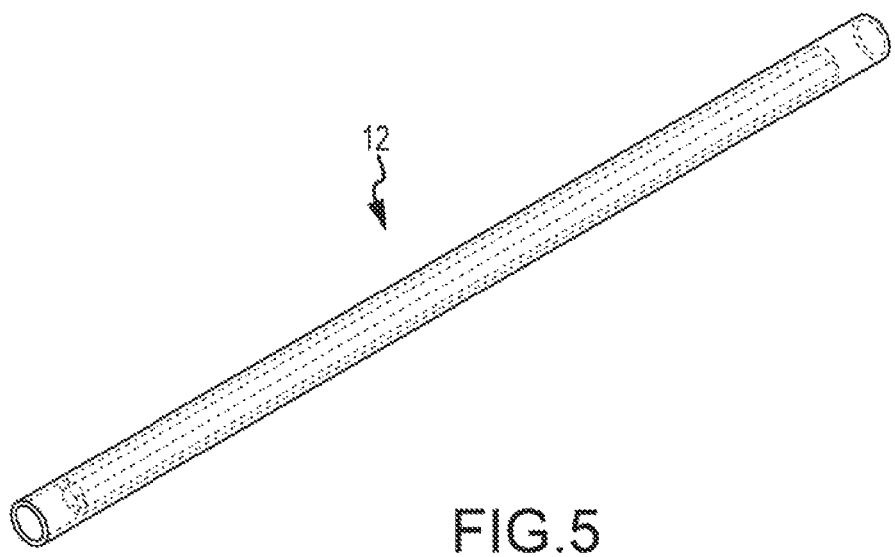
FIG. 5 is a transparent, isometric view of the deflectable catheter shaft section of FIG. 1, with various components of the catheter omitted for the purposes of clarity.

Referring now to FIG. 5, deflectable catheter shaft section 12 can be constructed of a series of polymer layer(s) and braid structure(s). In particular, one or more wires wound to form a cylindrical braid structure can substantially surround the plurality of lumens 24, 26, 28, 30, 32. In addition, a polymeric material, such as polyurethane, nylon, or various types of plastic materials such as polyether block amides offered under the trademark PEBAX®, which is a registered trademark of Arkema France, Puteaux, France, or any other suitable material, can also substantially surround the plurality of lumens 24, 26, 28, 30, 32. Regardless of the material used, the material must have the capability to be displaced or to shrink when subjected to a process, such as for example, a heating process that is performed.

The deflectable catheter shall section 12 can include one or more electrodes (such as, for example, ring electrodes 54) mounted on or affixed to the deflectable catheter shaft section 12. In these particular embodiments, an active outer surface of each electrode 54 can be configured for exposure to blood and/or tissue. Each electrode 54 may be assembled with the deflectable catheter shaft section 12 using any number of known processes. For instance, the electrodes 54 may be built into the deflectable catheter shall section 12 using a reflow process. In such a process, the electrodes 54 are placed at the appropriate/desired locations on the deflectable catheter shaft section 12, and then the tip deflectable catheter shaft section 12 is exposed to a heating process in which the electrodes 54 and polymeric material forming the deflectable catheter shaft section 12 become affixed or bonded together. Sufficiently sized aperture(s) are formed in the deflectable catheter shaft section 12 proximate to each electrode 54 in order to allow for wires (not shown) connected to the electrodes 54 to be threaded into first lumen 24 of deflectable catheter shaft section 12, for example, which may be configured for housing wiring for electrodes. The wires may extend through the lumen 24 of deflectable catheter shaft section 12 and may be connected to, for example, monitoring and/or recording devices and/or ablation devices associated with or connected to the catheter 10. These devices are typically located proximate to the handle assembly 22. The wires are typically pre-coated wires such that they are insulated from each other and other components in the catheter 10.

The mechanical properties of the deflectable catheter shaft section 12 can be varied by varying the properties of the cylindrical braid structure(s) and the polymeric material (e.g., dimension of the cylindrical braid structure and/or durometers of the polymers). Additionally, the mechanical properties of the deflectable catheter shaft section 12 can be varied along the length of the deflectable catheter shaft section 12 in accordance with some embodiments of the disclosure or can be substantially constant along the entire length of the deflectable catheter shaft section 12 in accordance with other embodiments of the disclosure.

Referring again to FIG. 1, proximal catheter shaft section 20 can also include one or more lumens (not shown). Generally, proximal catheter shaft section 20 can include a single lumen. The single lumen can be in communication with lumens 72, 74, 76, 78, 80 of shaft coupler 60, which are in turn in communication with lumens 24, 26, 28, 30, 32 of deflectable catheter shaft section 12. Proximal catheter shaft section 20 can also be constructed of a series of polymer layer(s) and braid structure(s). In particular, one or more wires wound to form a cylindrical braid structure can substantially surround the one or more lumens of proximal catheter shaft section 20. In addition, a polymeric material, such as polyurethane, nylon, or various types of plastic materials such as polyether block amides offered under the trademark PEBAX®, or any other suitable material, can also substantially surround the one or more lumens of proximal catheter shaft section 20. Regardless of the material used, the material must have capability to be displaced or to shrink when subjected to a process, such as for example, a heating process that is performed. The mechanical properties of the proximal catheter shaft section 20 can also be varied by varying the properties of the cylindrical braid structure(s) and the polymeric material (e.g., dimension of the cylindrical braid structure and/or durometers of the polymers). Additionally, the mechanical properties of the proximal catheter shaft section 20 can be varied along the length of the proximal catheter shaft section 20 in accordance with some embodiments of the disclosure or can be substantially constant along the entire length of the proximal catheter shaft section 20 in accordance with other embodiments of the disclosure.

Figure 6:
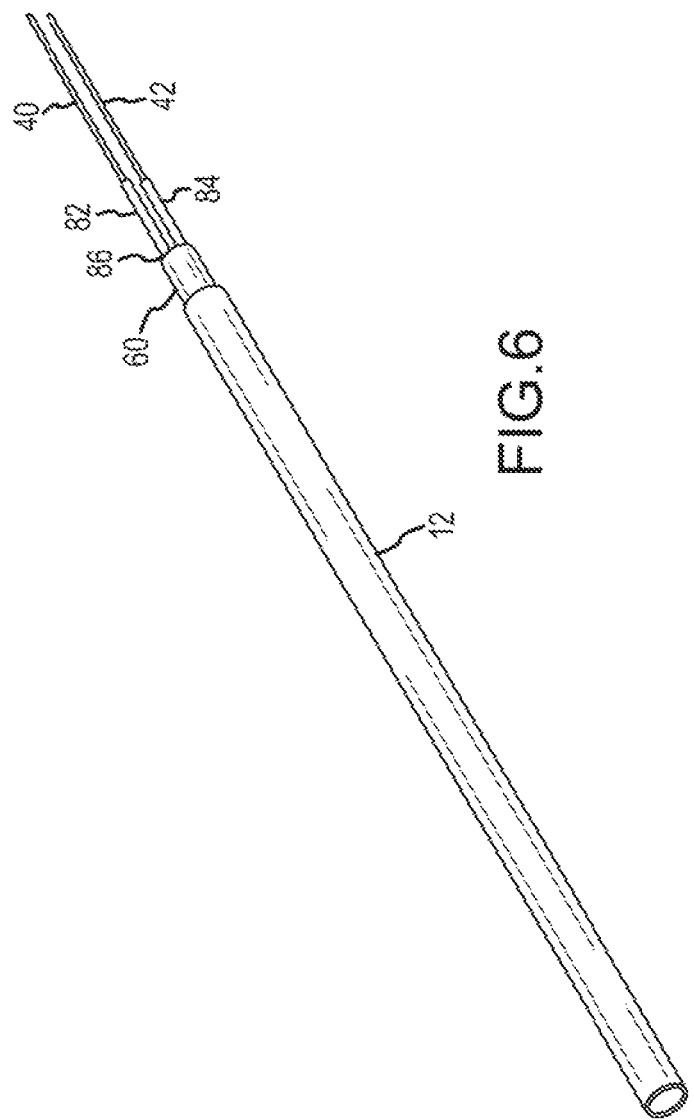
FIG. 6 is an isometric view of the deflectable catheter shall section of FIG. 1 and a shall coupler, pull wires, and compression coils in accordance with an embodiment of the invention.
Figure 7:
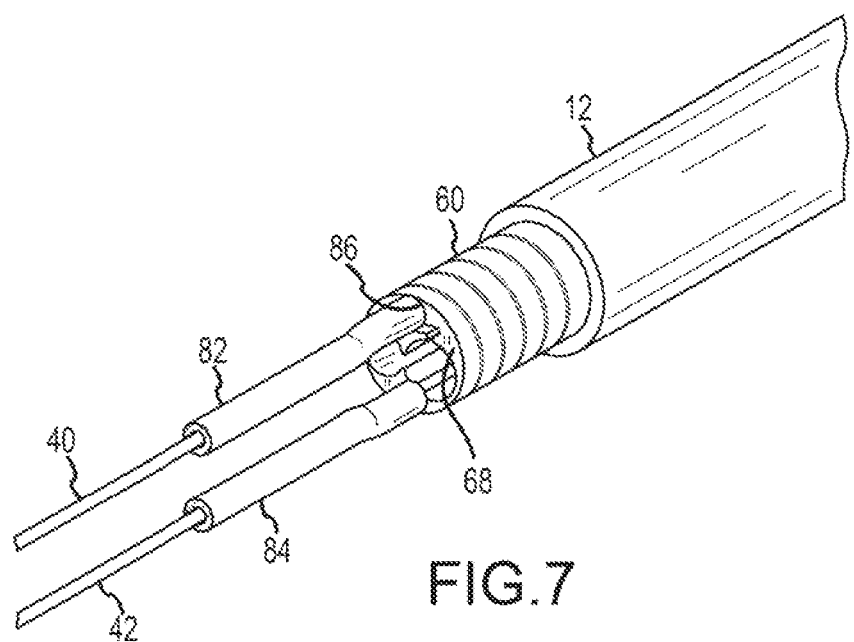
FIG. 7 is a partial, isometric view of the deflectable catheter shall section of FIG. 1 and a shall coupler, pull wires, and compression coils in accordance with an embodiment of the invention.

Referring now to FIGS. 6-8, the catheter 10 can include first and second tightly wound compression coils 82, 84 disposed in the proximal catheter shaft section 20 before engaging with the lumens 78, 80 of shaft coupler 60, which are in turn in communication with fourth and fifth lumens 30, 32, which extend through the deflectable catheter section 12. Each of the compression coils 82, 84 can comprise stainless steel in accordance with an embodiment of the invention. Each of the compression coils 82, 84 comprises a distal end 86 and a proximal end 88 (see FIG. 8). The outer diameter of the compression coils 82, 84 can be about 0.015 inches (0.38 mm) to about 0.030 inches (0.76 mm). The inner diameter of the compression coils 82, 84 can be about 0.004 inches (0.10 mm) to about 0.015 inches (0.38 mm). The compression coils 82, 84 are disposed over pull wires 40, 42. The pull wires 40, 42 extend from the pull ring 48 (FIG. 4A), through the delectable catheter shaft section 12, through the shaft coupler 60, through the proximal catheter shall section 20 to the handle assembly 22, but the compression cods 82, 84 generally extend only through the proximal catheter shaft section 20. The compression coils 82, 84 can extend the entire length of the proximal catheter shaft section 20 in accordance with some embodiments of the invention. In some embodiments, the one or more lumens of the proximal catheter shaft section 20 can be lined with liners (not shown) that serve the purpose of providing a lubricious surface (e.g., to allow for the sliding of the pull wires 40, 42). If provided, the liners may be constructed of a polymeric material, such as PTFE, or any other suitable material.

In order to provide the desired mechanical property of resisting compression during use, a catheter may incorporate a stainless steel compression coil embedded within an outer layer of the catheter shaft. However, in accordance with an embodiment of the present invention, the distal end 86 of each of the compression coils 82, 84 may not be embedded within an outer layer of the catheter shaft and may not otherwise be fixedly attached to the catheter 10 or components thereof. Instead, the compression coils 82, 84 may comprise floating members that are "sandwiched" in between components located at the distal end 86 and proximal end 88 of each of the compression coils 82, 84. By separating the compression coils 82, 84 from the catheter shaft itself, the catheter 10 can undergo bench testing for assessing deflection of the catheter 10 prior to formation of the catheter shaft through a reflow process as described in more detail hereinbelow. Moreover, by not fixedly attaching the compression coils 82, 84 to the catheter 10 or components thereof, the invention may exhibit improved ease of assembly. The distal end 86 of each compression coil 82, 84 can abut or be constrained by the proximal end 68 of the shaft coupler 60 as generally illustrated in FIGS. 6 and 7. As generally illustrated, the distal end 86 of each of the compression coils 82, 84 is not fixedly attached to the shaft coupler 60, but instead abuts or stops at or is constrained by an axial end surface of the shall coupler 60 as best shown in FIG. 7). Referring now to FIG. 8, the proximal end 88 of each compression coil 82, 84 can abut a distal end 90 of a portion of the handle assembly 22. Again, the proximal end 88 of each of the compression coils 82, 84 is not fixedly attached to the handle assembly 22, but instead abuts or stops at or is constrained by an axial end surface of the distal end 90 of a portion of the handle assembly 22. Each compression coil 82, 84 is tightly wound so it can bend, but is non-compressible.

Because the compression coils 82, 84 are non-compressible, tension on the pull wires 40, 42 will not translate into compressive tension on the proximal catheter shaft section 20. The compression coils 82, 84 are therefore configured to help assure that the proximal catheter shaft section 20 does not bend as a result of tension on the pull wires 40, 42 and that rotational control of the catheter 10 is not adversely affected when the pull wires 40, 42 are under tension. By separating the compression coils 82, 84 from the outer wall of the proximal catheter shaft section 20, the proximal catheter shaft section 20 is configured to provide pushability and torqueability for the catheter 10, without concomitant shaft compression and/or snaking.

Figure 9B:
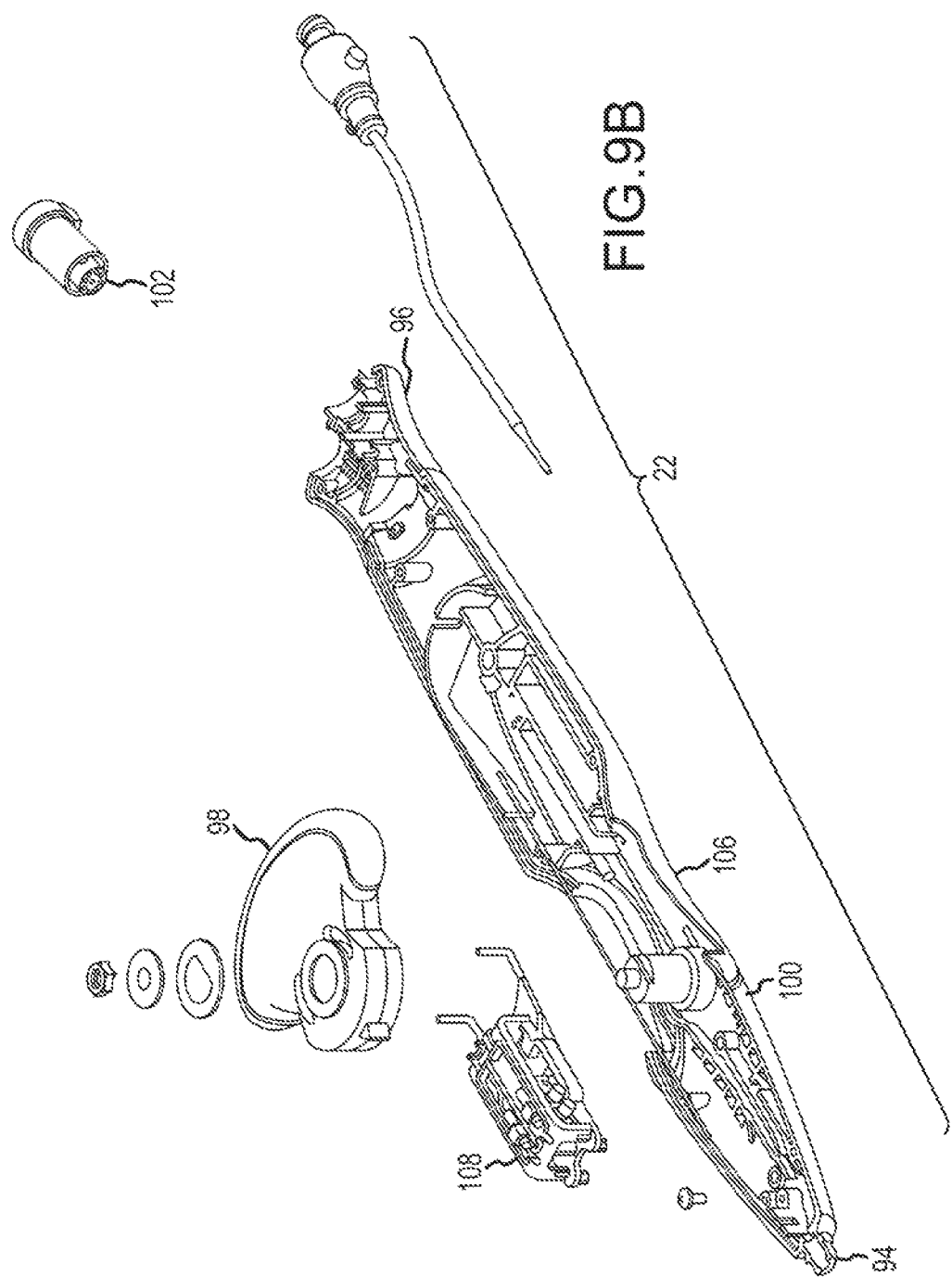
FIG. 9B is a partial, exploded view of the handle assembly of FIG. 9A.

Referring back to FIG. 1, the handle assembly 22 is coupled to the proximal catheter shaft section 20 at its proximal end (disposed within handle assembly 22 and not shown). The handle assembly 22 is operative to, among other things, effect movement (i.e., deflection) of the deflectable catheter shaft section 12. The handle assembly 22 includes a distal end 94 and a proximal end 96. Referring now to FIGS. 9A and 9B and as will be described in greater detail below, the handle assembly 22 includes an actuator 98 that can be selectively manipulated to cause deflectable catheter shaft section 12 to deflect in one or more directions (e.g., up, down, left, and right). Deflectable catheter shaft section 12 may be configured for uni-directional deflection in accordance with some embodiments of the invention and may be configured for bi-directional deflection in accordance with other embodiments of the invention.

Still referring to FIGS. 9A and 9B, the handle assembly 22 includes an actuator 98, an upper grip portion 101 (see FIG. 1) and a lower grip portions 100, an electrical plug 102 at the proximal end 96 of the handle assembly 22, and a strain relief 104 at the distal end 94 of the handle assembly 22. The upper and lower grip portions 101, 100, when assembled, define a space 106 that extends laterally through the grip portions 101, 100. The actuator 98 is pivotally coupled to the grip portions 100 and resides in the space 106. The actuator 98 may pivotally displace laterally relative to the grip portions 100 through the space 106. Such pivotal displacement of the actuator 98 allows medical personnel to bi-directionally deflect the deflectable catheter shaft section 12. The pull wires 40, 42 extend from the pull ring 48 (see FIG. 4A), through the deflectable catheter shaft section 12, through the shaft coupler 60, through the proximal catheter shaft section 20, and into the handle assembly 22 to couple to an actuation mechanism 108 of the actuator 98 as will be described in more detail hereinbelow. The upper and lower grip portions 101, 100 are adapted to matingly couple with each other and serve as an enclosure and mounting base for the actuation mechanism 108 mounted in a distal portion of the handle assembly 22. The electrical plug 102 is adapted to be connected to a monitoring or a recording or an ablation device. The electrical plug 102 is mounted in a proximal end assembly that serves as the proximal end 96 of the handle assembly 22. The structure and function of the actuation mechanism 108 and the actuator 98 is described in detail in U.S. Pat. No. 7,465,288, which is hereby incorporated by reference as though set forth in its entirety.

The catheter 10 may include any number of other elements such as, for example and without limitation, thermocouples, thermistor temperature sensors, etc. for monitoring the temperature of targeted tissue and controlling the temperature.

Figure 10A:
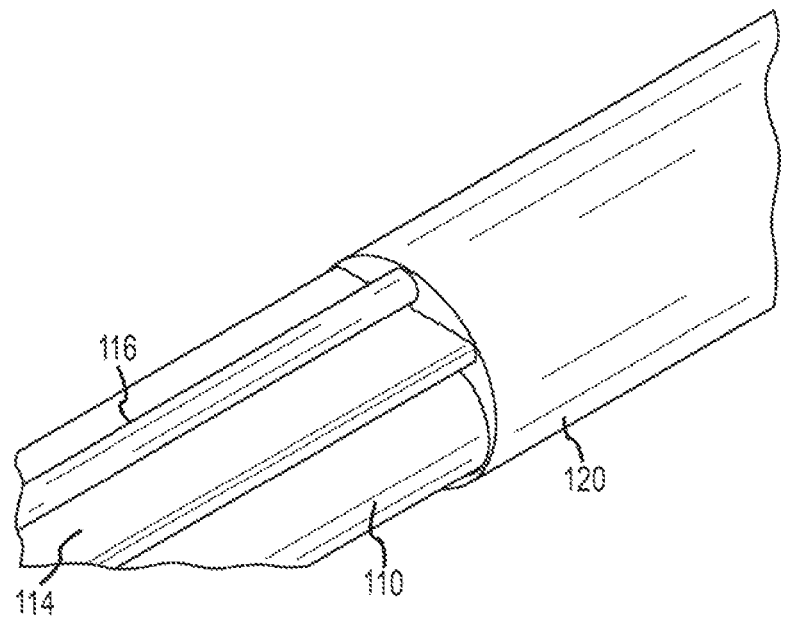
FIGS. 10A-10C are partial, isometric views of mandrels and a mandrel alignment tool for manufacturing the deflectable catheter shaft section of FIG. 1 in accordance with an embodiment of the invention.
Figure 10B:
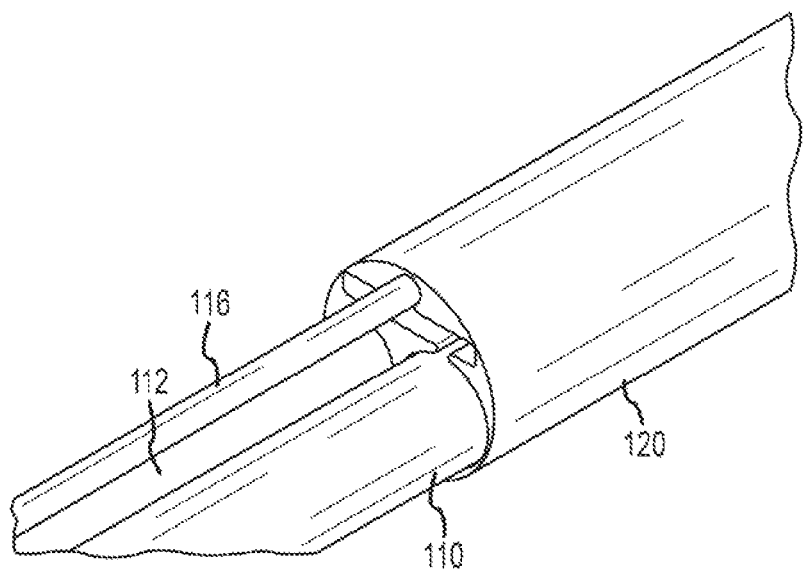
Figure 10C:
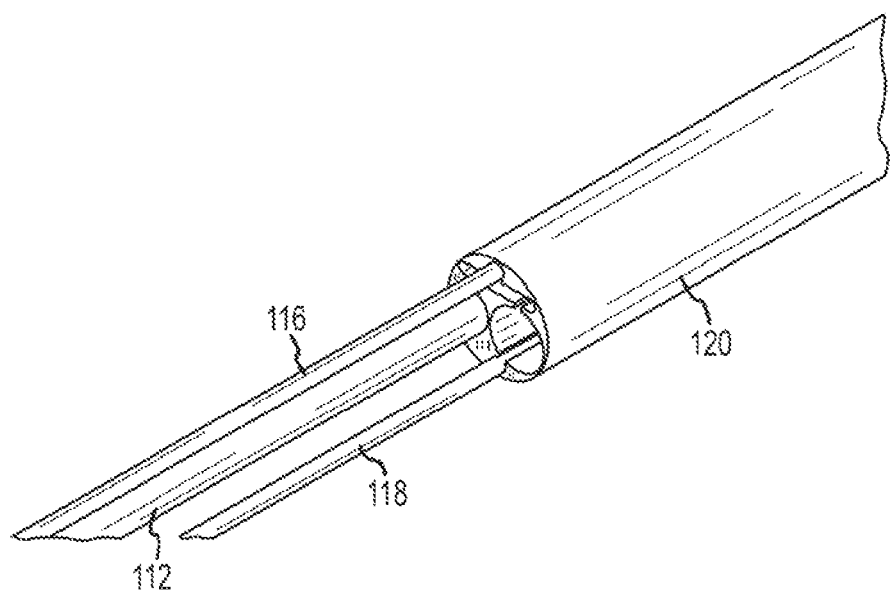

With reference to FIGS. 10A-15, a method of manufacturing the deflectable catheter shaft section 12 will now be described. The exemplary method comprises a first step of providing a fluid lumen mandrel 110 (FIGS. 10A and 10B), an electrical lumen mandrel 112 (FIGS. 10B and 10C), a planarity wire mandrel 114 (FIG. 10A), and two pull wire mandrels 116, 118 (FIGS. 10A-10C). The exemplary method further comprises a second step of providing a mandrel alignment tool 120.

Figure 11:
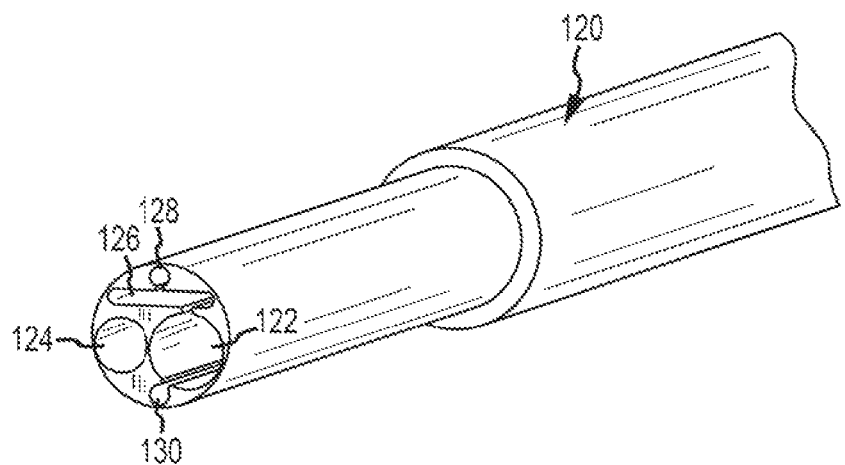
FIG. 11 is a partial, isometric view of a mandrel alignment tool for manufacturing the deflectable catheter shaft section of FIG. 1 in accordance with an embodiment of the invention.
Figure 12:
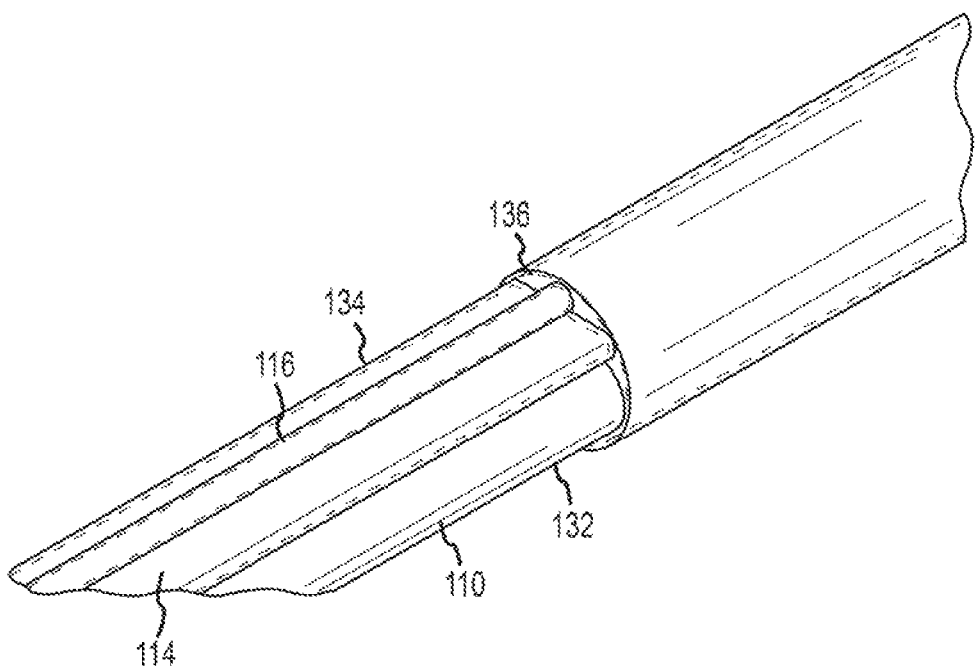
FIG. 12 is a fragmentary, isometric view of mandrels with surrounding polymeric tubes over them for manufacturing the deflectable catheter shaft section of FIG. 1 in accordance with an embodiment of the invention.

Referring in particular to FIG. 11, the mandrel alignment tool 120 comprises a plurality of slots 122, 124, 126, 128, 130 each corresponding to one of the fluid lumen mandrel 110, the electrical lumen mandrel 112, the planarity wire mandrel 114, and the two pull wire mandrels 116, 118, respectively. The mandrel alignment tool 120 can be formed by wire cutting from slot to slot in an exemplary method of manufacturing the catheter 10. The exemplary method further comprises a third step of placing polymeric tubes (e.g., polymeric tubes 132, 134, 136 as generally illustrated in FIG. 12) over each of the mandrels 110, 112, 114, 116, 118 so that the polymeric tubes externally surround each of the mandrels 110, 112, 114, 116, 118. Although FIG. 12 only shows polymeric tubes over mandrels 110, 114, and 116, those of ordinary skill in the art will recognize that polymeric tubes are disposed over each of the mandrels. The polymeric tubes (e.g., polymeric tubes 132, 134, 136) can comprise PTFE in accordance with an embodiment of the invention.

Figure 13:
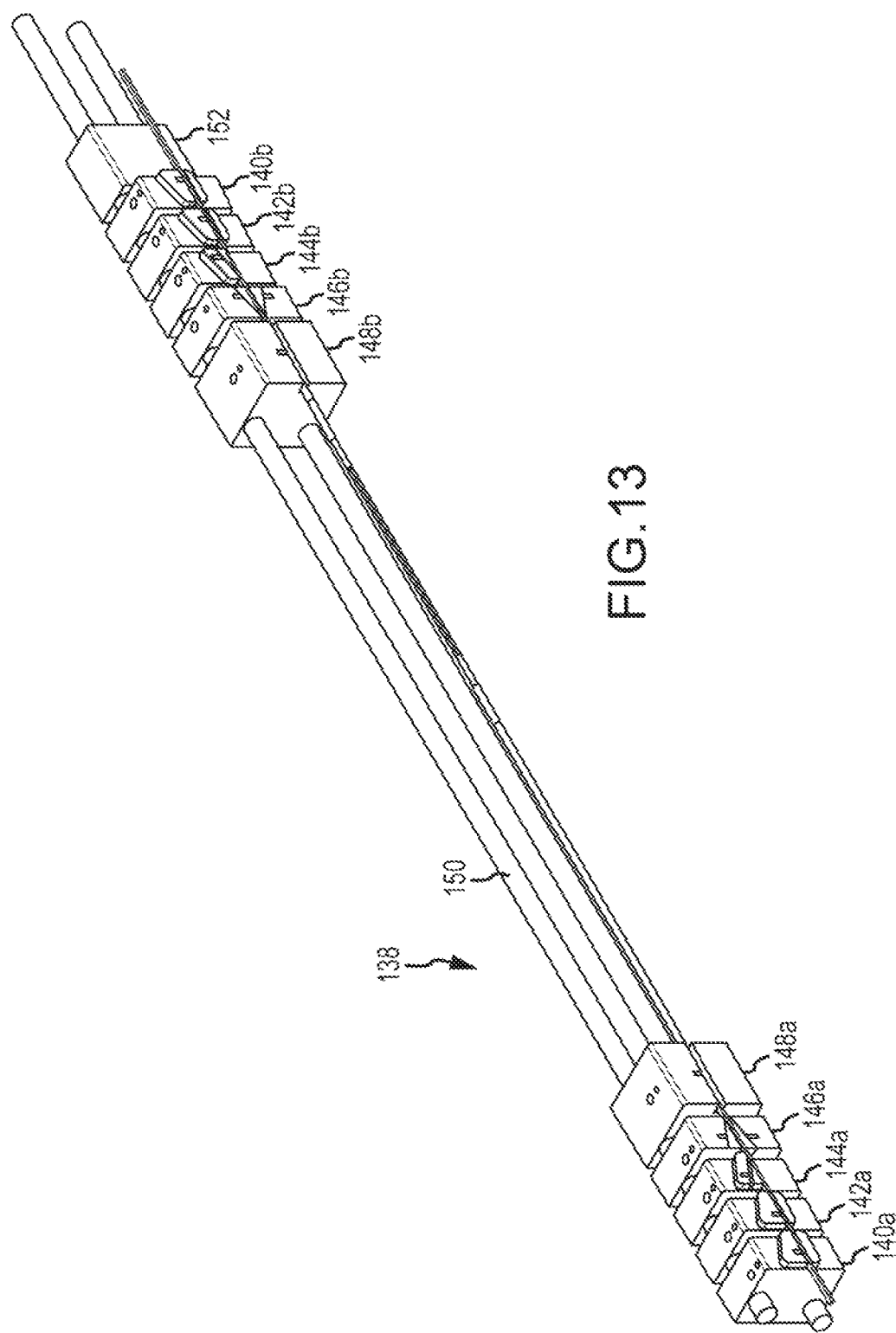
FIG. 13 is an isometric view of tooling for manufacturing the deflectable catheter shall section of FIG. 1 in accordance with an embodiment of the invention.
Figure 14:
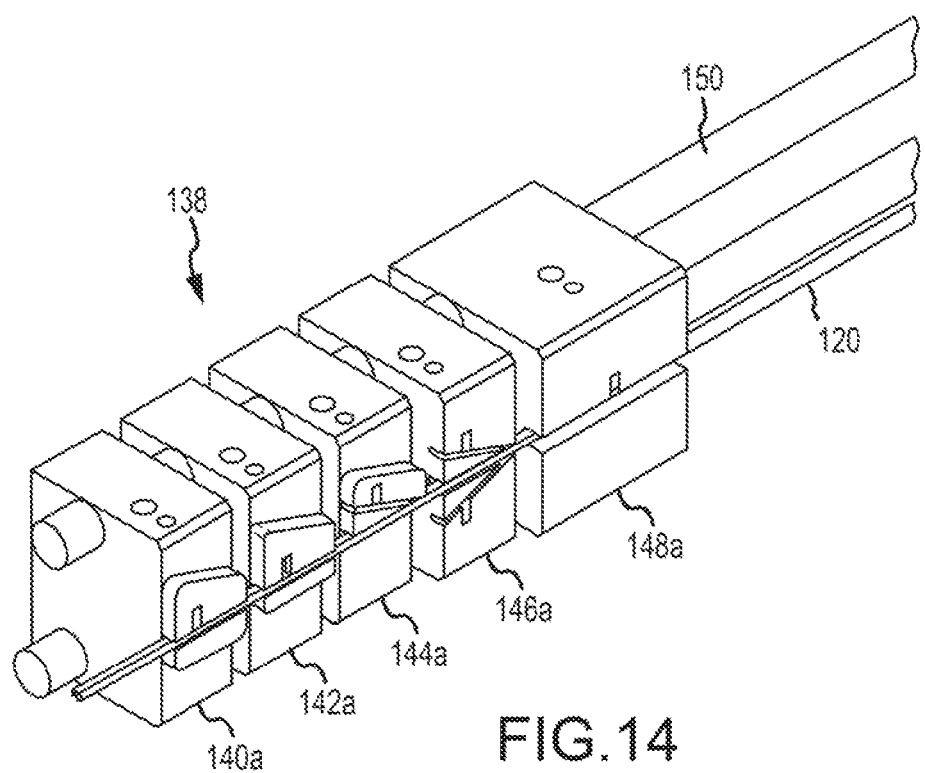
FIG. 14 is a partial, isometric view of tooling for manufacturing the deflectable catheter shall section of FIG. 1 in accordance with an embodiment of the invention.
Figure 15:
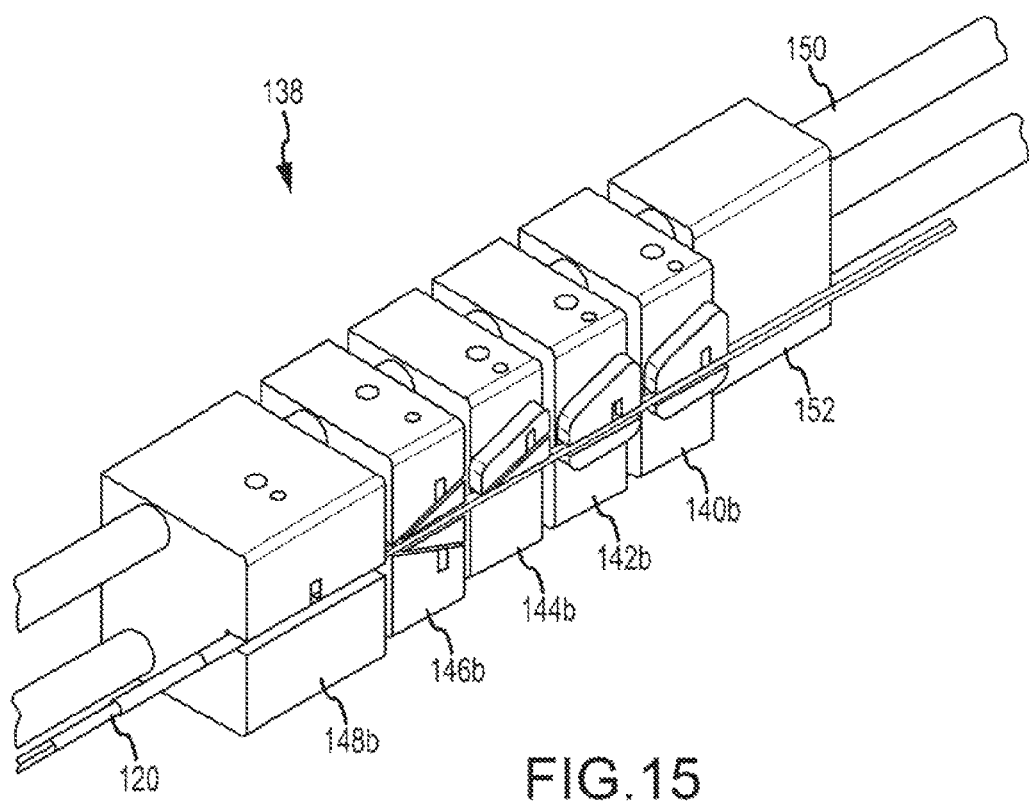
FIG. 15 is a partial, isometric view of tooling for manufacturing the deflectable catheter shaft section of FIG. 1 in accordance with an embodiment of the invention.

Referring now to FIGS. 13-15 in particular, the exemplary method comprises a fourth step of providing tooling 138 configured to hold the mandrel alignment tool 120. In an exemplary embodiment, the tooling 138 comprises live pairs of opposing clamps or tensioning blocks 140*a*, 140*b*; 142*a*, 142*b*; 144*a*, 144*b*; 146*a*, 146*b*; and 148*a*, 148*b*. Each pair of opposing clamps or tensioning blocks 140*a*, 140*b*; 142*a*, 142*b*, 144*a*, 144*b*; 146*a*, 146*b*; and 148*a*, 148*b* corresponds to one of the mandrels 110, 112, 114, 116, 118, and the mandrel alignment tool 120 respectively. The opposing clamps or tensioning blocks 140*a*, 140*b*; 142*a*, 142*b*; 144*a*, 144*b*; 146*a*, 146*b*; and 148*a*, 148*b* are disposed at opposite ends of at least one elongate member 150. The elongate member 150 is configured for facilitating placement of the clamps or tensioning blocks 140*a*, 140*b*; 142*a*, 142*b*; 144*a*, 144*b*; 146*a*, 146*b*; and 148*a*, 148*b* in a predetermined, select position relative to each other-A first set of clamps or tensioning blocks 140*a*, 142*a*, 144*a*, 146*a*, 148*a* are in a fixed position and are generally illustrated in FIG. 14. A second set of clamps or tensioning blocks 140*b*, 142*b*, 144*b*, 146*b*, 148*b* are configured for tensioning. This second set of clamps or tensioning blocks 140*b*, 142, 144*b*, 146*b*, 148*b* are configured to allow each mandrel 110, 112, 114, 116, 118 to be placed under tension and then released from tension as desired. The tooling 138 can further comprise a compression block 152 at one end of the elongate member 150. The compression block 152 can be disposed on the elongate member 150 near the second set of clamps or tensioning blocks 140*b*, 142*b*, 144*b*, 146*b*, 148*b*.

The exemplary method further comprises a fifth step of clamping mandrels 110, 112, 114, 116, 118 and the surrounding polymeric tubes into place on the tooling 138. In particular, the mandrel alignment tool 120 may be placed at both ends of the tooling 138 to facilitate proper placement or alignment of the mandrels 110, 112, 114, 116, 118 in the tooling 138. The mandrels 110, 112, 114, 116, 118 may be placed within slots located within each of the opposing clamps or tensioning blocks 140*a*, 140*b*; 142*a*, 142*b*; 144*a*, 144*b*; 146*a*, 146*b*; and 148*a*, 148*b* and each mandrel 110, 112, 114, 116, 118 may be clamped in place into one pair of the opposing clamps or tensioning blocks 140*a*, 140*b*; 142*a*, 142*b*; 144*a*, 144*b*; 146*a*, 146*b*; and 148*a*, 148*b*.

The exemplary method further comprises a sixth step of tensioning each mandrel 110, 112, 114, 116, 118 (e.g., through use of tension block 152) and a seventh step of releasing tension of each mandrel 110, 112, 114, 116, 118 (e.g., through release of tension block 152). The exemplary method further comprises an eighth step of placing (e.g., sliding) the cylindrical braid structure described hereinabove over the group of mandrels 110, 112, 114, 116, 118 and corresponding surrounding polymeric (e.g., PTFE) tithes and stretching the cylindrical braid structure tight over the group of mandrels 110, 112, 114, 116, 118 and corresponding surrounding polymeric tubes.

The exemplary method further comprises the ninth step of placing (e.g., sliding) one or more polymeric tubes over the cylindrical braid structure. The one or more polymeric tubes slid over the cylindrical braid structure can comprise polyurethane, nylon, or various types of plastic materials such as polyether block amides offered under the trademark PEBAX®, or airy other suitable material, in accordance with various embodiments of the invention. The mechanical properties of the deflectable catheter shall section 12 can be varied by varying the properties the polymeric materials (e.g., durometers of the polymeric materials utilized).

The exemplary method further comprises the tenth step of placing (e.g., sliding) a heat shrink tube (not shown) over the one or more polymeric tubes such that both ends of the heat shrink tube are covering the mandrel alignment tools 120 at both ends of the tooling 138. The exemplary method comprises the eleventh step of pre-shrinking the heat shrink tube. The step of pre-shrinking the heat shrink tube can be accomplished with a heat gun or other heat source in accordance with various embodiments of the invention. The exemplary method further comprises the twelfth step of placing the tooling 138 and accompanying mandrels 110, 112, 114, 116, 118, polymeric (e.g., PTFE) tubes, cylindrical braid structure, polymeric (e.g., polyurethane, nylon, polyether block amides available under the brand name PEBAX®) tubes, and heat shrink tubing into an oven or other heat source and subjecting them to a heating process that includes reflowing a portion of the deflectable catheter shall section 12. The temperature of the oven and the length of the time for the heating process can vary in accordance with various embodiments of the invention. The exemplary method further comprises the thirteenth step of removing the mandrels 110, 112, 114, 116, 118 and heat shrink tubing in accordance with methods known by those of ordinary skill in the art. The exemplary method further comprises the fourteenth step of trimming the deflectable catheter shaft section 12 to a predetermined, select length.

The exemplary method can further comprise additional steps of inserting one or more components into one or more lumens in the deflectable catheter shaft section 12 that were formed. In an exemplary embodiment, the components inserted and disposed within the lumens can include, as described above, at least one electrode wire, as planarity wire 34, and/or at least one pull wire 40, 42. The components within the deflectable catheter shaft section 12 can take the form of any number of different or additional articles/devices typically present in catheters used for diagnostic or therapeutic purposes (e.g., wires corresponding to temperature sensing elements, etc.).

Although at least one embodiment of a deflectable catheter shaft section, a catheter incorporating such a deflectable catheter shaft section, and a method of manufacturing such a deflectable catheter shaft section have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to ad the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter comprising the following:
   an elongated body extending along a body longitudinal axis, the elongated body comprising a proximal catheter shaft section and a distal, deflectable catheter shaft section;
   first and second pull wires, wherein each of the first and second pull wires comprises a proximal end and a distal end, and wherein each of the first and second pull wires extends along the proximal catheter shaft section and along the deflectable catheter shaft section;
   first and second compression coils each disposed over one of the first and second pull wires, respectively, along the proximal catheter shaft section, and wherein each of the first and second compression coils comprises a proximal end and a distal end; and
   a plurality of shaft lumens extending along the deflectable catheter shaft section, wherein at least one of the plurality of shaft lumens is abutting at least another one of the plurality of shaft lumens,
   wherein the deflectable catheter shaft section comprises a polymeric material and wherein the polymeric material fully forms and substantially surrounds each of the plurality of shaft lumens.

2. The catheter of claim 1, wherein each of the plurality of lumens is abutting at least another one of the plurality of lumens.

3. The catheter of claim 1, wherein a first lumen and a second lumen of the plurality of lumens are less than about 0.015 inches from each other.

4. The catheter of claim 1, wherein each of the plurality of lumens is less than about 0.015 inches from another of the plurality of lumens.

5. The catheter of claim 1, wherein a first lumen and a second lumen of the plurality of lumens have partially merged boundaries.

6. The catheter of claim 1 further comprising the following:
   a handle assembly at a proximal end of the proximal catheter shaft section, wherein a portion of the handle assembly presses against the proximal ends of the first and second compression coils; and
   a shaft coupler extending proximally from a proximal end of the deflectable catheter shaft section, wherein a proximal portion of the shaft coupler presses against the distal ends of the first and second compression coils.

7. The catheter of claim 1 further comprising a plurality of liners including at least one liner for each of the plurality of shaft lumens, wherein each of the plurality of liners comprises a polymeric tube.

8. The catheter of claim 1 further comprising a plurality of liners, wherein each liner of the plurality of liners is constructed from material selected from the group consisting of polyurethane, nylon, polyether block amides, and polytetrafluoroethylene.

9. The catheter of claim 1, wherein the plurality of shaft lumens further comprises the following:
   diametrically-opposed first and second pull wire lumens, each pull wire lumen extending substantially parallel to the body longitudinal axis; and
   diametrically-opposed first and second larger lumens, each larger lumen extending substantially parallel to the body longitudinal axis.

10. The catheter of claim 9, wherein the first and second pull wire lumens are symmetrically disposed on either side of a first longitudinally-extending plane bisecting the deflectable catheter shaft section into a first hemicylindrical portion and a second hemicylindrical portion.

11. The catheter of claim 10, wherein the first and second larger lumens are symmetrically disposed on either side of a second longitudinally-extending plane bisecting the deflectable catheter shaft section into a third hemicylindrical portion and a fourth hemicylindrical portion, and wherein the first longitudinally extending plane is rotated 90 degrees relative to the second longitudinally extending plane.

12. The catheter of claim 1 further comprising a tip assembly disposed at a distal end of the deflectable catheter shaft section.

13. The catheter of claim 12 further comprising a handle assembly comprising an actuator configured to effect movement of the deflectable catheter shaft section.

14. The catheter of claim 13 further comprising a pull ring disposed adjacent to the distal end of the deflectable catheter shaft section, wherein the distal end of the first pull wire and the distal end of the second pull wire are attached to diametrically opposite locations on the pull ring, wherein the first and second pull wires extend from the pull ring toward the handle assembly.

15. A catheter comprising the following:
an elongated body extending along a body longitudinal axis, the elongated body comprising a proximal catheter shaft section and a distal, deflectable catheter shaft section;
first and second pull wires, wherein each of the first and second pull wires comprises a proximal end and a distal end, and wherein each of the first and second pull wires extends along the proximal catheter shaft section and along the deflectable catheter shaft section;
first and second compression coils each disposed over one of the first and second pull wires, respectively, along the proximal catheter shaft section, and wherein each of the first and second compression coils comprises a proximal end and a distal end; and
a plurality of shaft lumens extending along the deflectable catheter shaft section, wherein a first lumen and a second lumen of the plurality of lumens are connected to each other,
wherein the deflectable catheter shaft section comprises a polymeric material and wherein the polymeric material fully forms and substantially surrounds each of the plurality of shaft lumens.

16. The catheter of claim 15, wherein the connected first and second lumens are each generally round in cross-sectional shape.

17. The catheter of claim 16, wherein the connected first and second lumens define a figure eight cross-sectional shape.

18. The catheter of claim 17 further comprising a plurality of liners including at least one liner for each of the plurality of shaft lumens.

19. The catheter of claim 17, wherein the connected first and second lumens are lined with a polymeric tube.

20. The catheter of claim 17, wherein the figure-eight cross sectional shape of the connected first and second lumens further defines a waist where the first and second lumens connect, wherein the plurality of lumens further comprises a first pull wire lumen and a second pull wire lumen, and wherein the first pull wire lumen is located on one side of the waist and the second pull wire lumen is located on the opposite side of the waist.

21. The catheter of claim 20, wherein the first and second pull wire lumens are symmetrically disposed on either side of a first longitudinally-extending plane bisecting the deflectable catheter shaft section into a first hemicylindrical portion and a second hemicylindrical portion.

22. The catheter of claim 21, wherein the connected first and second lumens are symmetrically disposed on either side of a second longitudinally-extending plane that (a) contains the waist of the figure-eight cross sectional shape and (b) bisects the deflectable catheter shaft section into a third hemicylindrical portion and a fourth hemicylindrical portion, and wherein the second longitudinally extending plane is rotated 90 degrees relative to the first longitudinally extending plane.

* * * * *